United States Patent
Oz et al.

(10) Patent No.: US 9,427,237 B2
(45) Date of Patent: Aug. 30, 2016

(54) METHOD AND APPARATUS FOR CIRCULATORY VALVE REPAIR

(71) Applicant: The Trustees of Columbia University in the City of New York, New York, NY (US)

(72) Inventors: Mehmet C. Oz, Cliffside Park, NJ (US); Gerald M. Lemole, Huntingdon Valley, CT (US); Alan Lotvin, Upper Saddle River, NJ (US); Juan P. Umana, New York, NY (US); William Allen, Stratford, CT (US); Howard P. Levin, Teaneck, NJ (US)

(73) Assignee: The Trustees Of Columbia University In The City Of New York, New York, NY (US)

( * ) Notice: Subject to any disclaimer, the term of this patent is extended or adjusted under 35 U.S.C. 154(b) by 182 days.

(21) Appl. No.: 14/225,750

(22) Filed: Mar. 26, 2014

(65) Prior Publication Data

US 2014/0296878 A1    Oct. 2, 2014

Related U.S. Application Data

(60) Continuation of application No. 13/370,690, filed on Feb. 10, 2012, now Pat. No. 8,721,665, which is a continuation of application No. 12/209,336, filed on Sep. 12, 2008, now Pat. No. 8,133,239, which is a division of application No. 10/883,412, filed on Jun. 30, 2004, now Pat. No. 7,509,959, which is a continuation of application No. 09/950,163, filed on Oct. 15, 2002, now Pat. No. 7,758,596, which is a continuation of application No. 09/747,558, filed on Dec. 23, 2000, now abandoned, which is a continuation of application No. 09/254,111, filed as application No. PCT/US98/13240 on Jun. 25, 1998, now Pat. No. 6,269,819.

(60) Provisional application No. 60/051,078, filed on Jun. 27, 1997.

(51) Int. Cl.
| | |
|---|---|
| A61B 17/10 | (2006.01) |
| A61B 17/08 | (2006.01) |
| A61B 17/128 | (2006.01) |
| A61B 17/064 | (2006.01) |
| A61B 17/122 | (2006.01) |
| A61B 17/068 | (2006.01) |
| A61B 17/00 | (2006.01) |
| A61F 2/24 | (2006.01) |

(52) U.S. Cl.
CPC ......... *A61B 17/1285* (2013.01); *A61B 17/064* (2013.01); *A61B 17/0644* (2013.01); *A61B 17/0686* (2013.01); *A61B 17/08* (2013.01); *A61B 17/10* (2013.01); *A61B 17/122* (2013.01); *A61B 2017/00243* (2013.01); *A61B 2017/0649* (2013.01); *A61F 2/2427* (2013.01)

(58) Field of Classification Search
CPC .......... A61B 17/1285; A61B 17/0686; A61B 17/122; A61B 17/064; A61B 17/10; A61B 17/0644; A61B 17/08; A61B 2017/00243; A61B 2017/0649; A61F 2/2427
See application file for complete search history.

(56) References Cited

U.S. PATENT DOCUMENTS

| | | | | |
|---|---|---|---|---|
| 4,038,987 | A * | 8/1977 | Komiya | A61B 17/122 606/142 |
| 4,706,668 | A * | 11/1987 | Backer | A61B 17/1285 606/142 |
| 8,721,665 | B2 * | 5/2014 | Oz | A61B 17/064 606/142 |

*Primary Examiner* — Julian W Woo
(74) *Attorney, Agent, or Firm* — Reed Smith LLP; Lisa A. Chiarini

(57) ABSTRACT

An apparatus for the repair of a cardiovascular valve has leaflets comprising a grasper capable of grabbing and co-apting the leaflets of the valve. In a preferred embodiment, the grasper has jaws that grasp and immobilize the leaflets, and then a fastener is inserted to co-apt the leaflets. The apparatus is particularly useful for repairing mitral valves to cure mitral regurgitation.

17 Claims, 13 Drawing Sheets

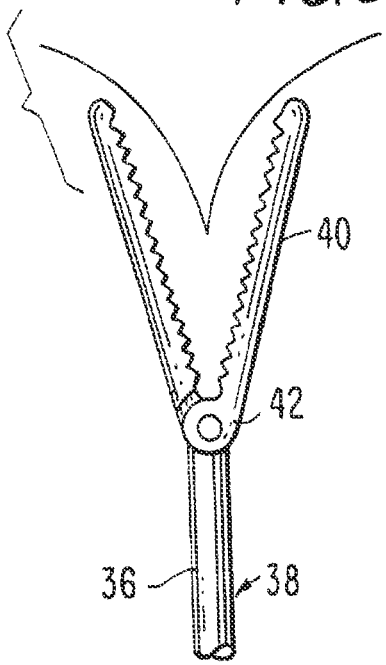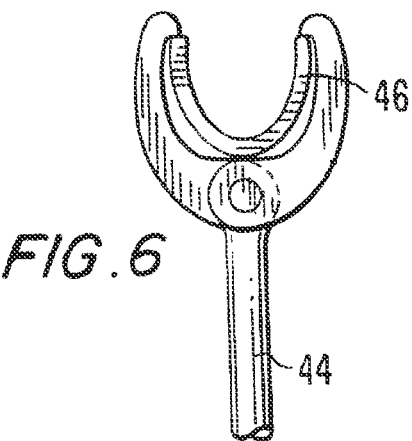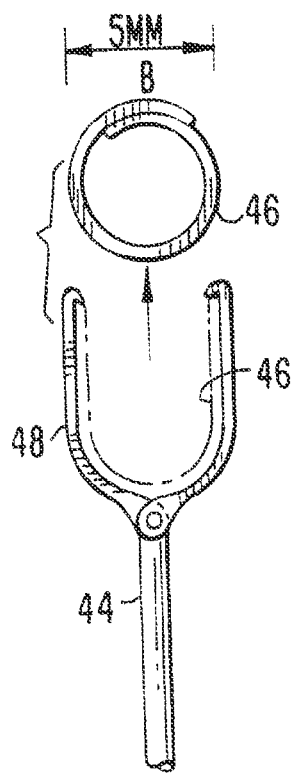

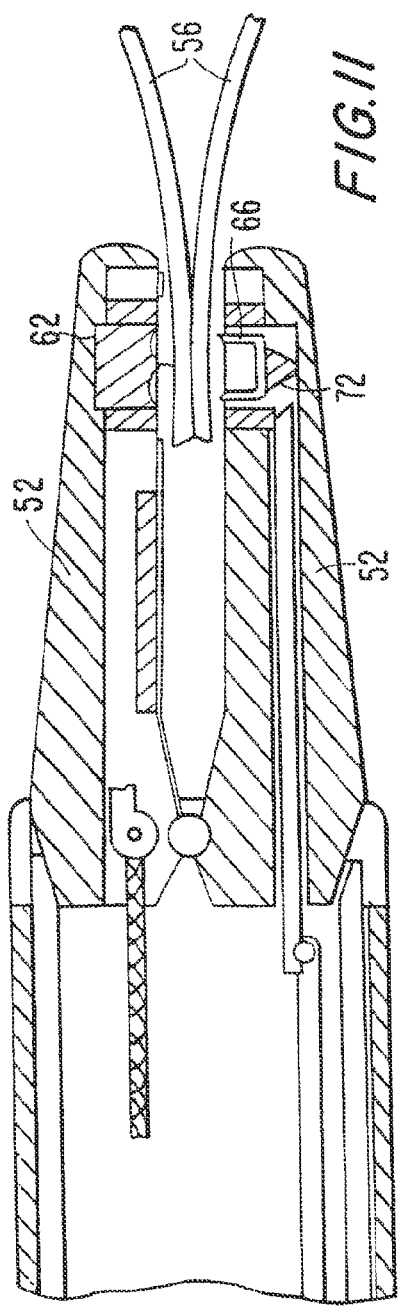
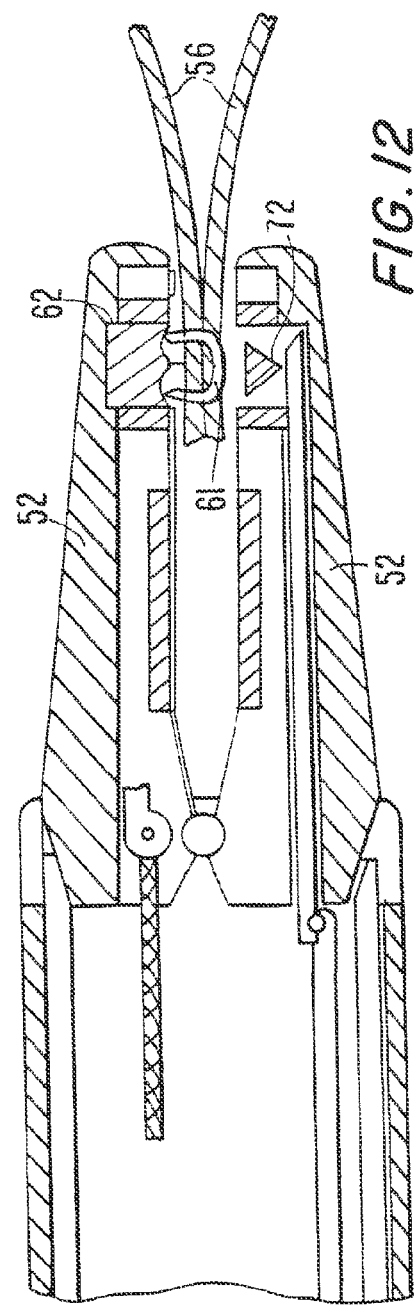

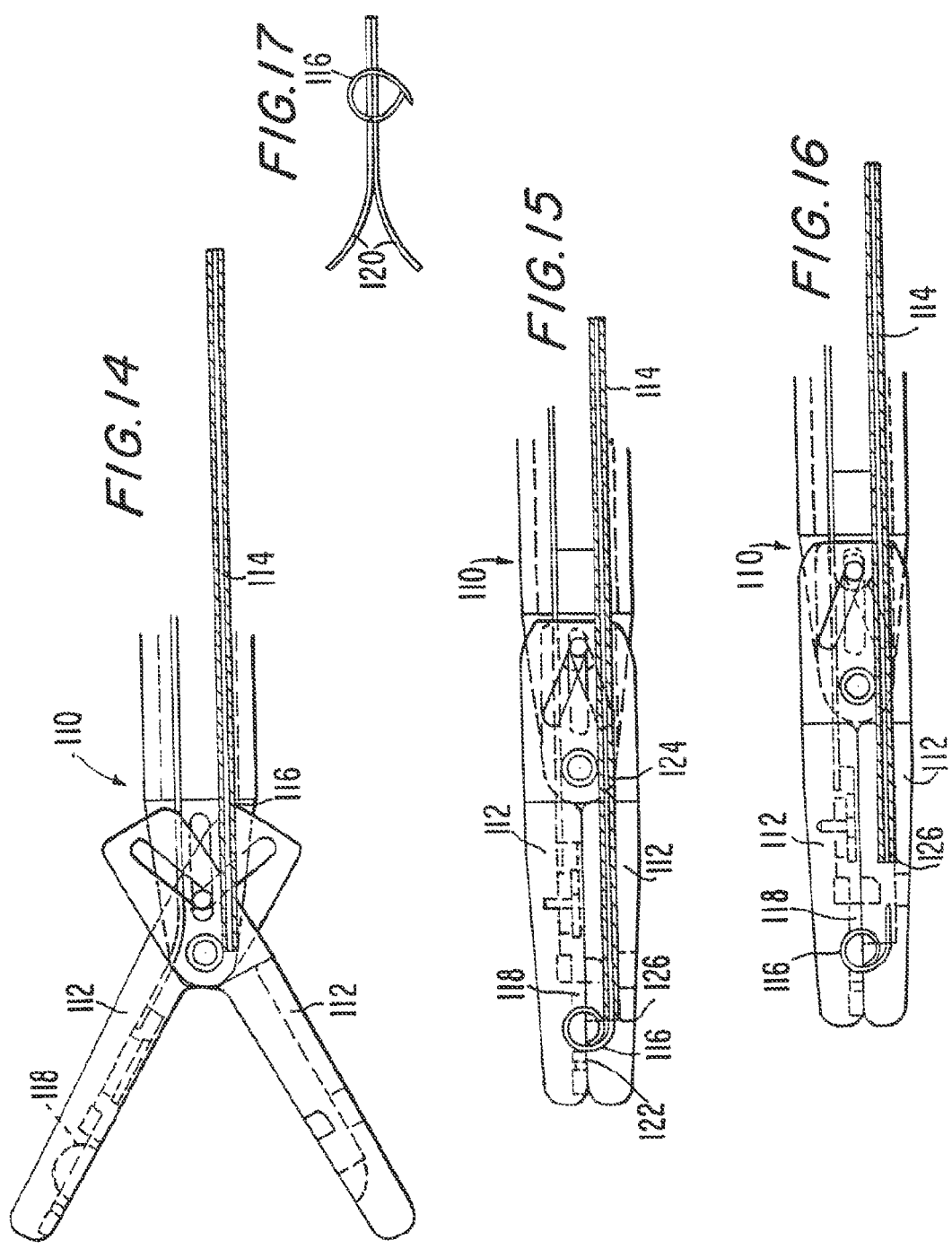

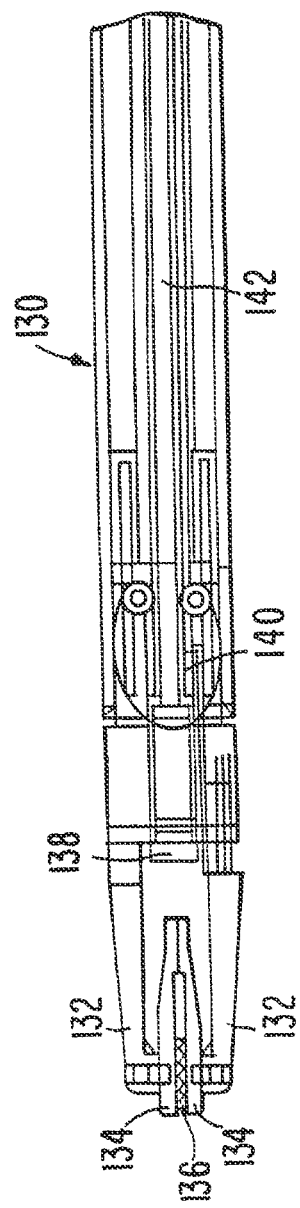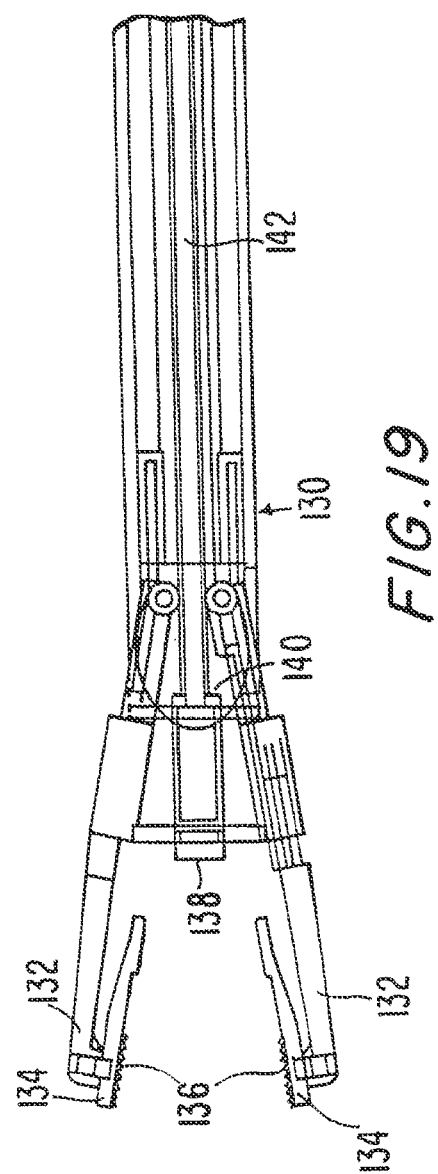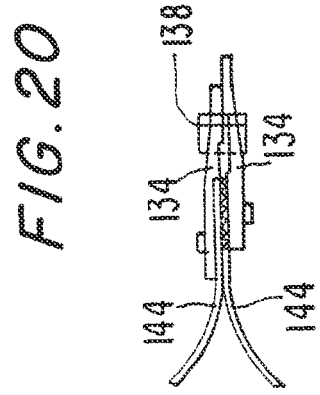

METHOD AND APPARATUS FOR CIRCULATORY VALVE REPAIR

CROSS-REFERENCE TO RELATED APPLICATIONS

This application is a continuation-in-part of commonly assigned U.S. patent application Ser. No. 13/370,690, filed Feb. 10, 2012, now U.S. Pat. No. 8,721,665, which is in turn a continuation of commonly assigned U.S. patent Ser. No. 12/209,336, filed Sep. 12, 2008, now U.S. Pat. No. 8,133,239, which is in turn a divisional of commonly assigned U.S. patent application Ser. No. 10/883,412, filed Jun. 30, 2004, now U.S. Pat. No. 7,509,959, which is in turn a continuation of commonly assigned U.S. patent application Ser. No. 09/950,163, filed Oct. 15, 2002, now U.S. Pat. No. 7,758,596, which in turn is a continuation of commonly assigned U.S. patent application Ser. No. 09/747,558, filed Dec. 23, 2000, now abandoned, which in turn is a continuation of commonly assigned U.S. patent application Ser. No. 09/254,111, filed Feb. 25, 1999, now U.S. Pat. No. 6,269,819, which in turn is a National Phase of commonly assigned PCT Patent Application No. PCT/US98/13240, filed Jun. 25, 1998, which is based upon and claims the benefit of the priority of U.S. Provisional Patent Application No. 60/051,078, filed Jun. 27, 1997, each of which is incorporated herein in its entirety.

FIELD OF THE INVENTION

The present invention relates generally to the field of circulatory valve repair. More particularly, the present invention relates to the field of the repair of heart valves and specifically for the repair of mitral heart valves, for patients suffering from mitral regurgitation.

BACKGROUND OF THE INVENTION

There are four valves in the heart that serve to direct the flow of blood through the two sides of the heart in a forward direction. On the left side, the mitral and aortic valves direct oxygenated blood coming from the lungs, through the left side of the heart, into the aorta for distribution to the body. On the right side, the tricuspid valve, located between the right atrium and the right ventricle, and the pulmonary valve, located between the right ventricle and the pulmonary artery, direct de-oxygenated blood coming from the body, through the right side of the heart, into the pulmonary artery for distribution to the lungs. The anatomy of the heart and the structure and terminology of heart valves are described and illustrated in detail in numerous reference works on anatomy and cardiac surgery, including standard texts such as *Surgery of the Chest* (Sabiston and Spencer, eds., Saunders Publ., Philadelphia) and *Cardiac Surgery* by Kirklin and Barrett-Boyes, Pathology and Abnormalities of Heart Valves, incorporated herein by reference.

All four heart valves are passive structures in that they do not themselves expend any energy and do not perform any active contractile function. They consist of moveable "leaflets" that are designed simply to open and close in response to differential pressures on either side of the valve. The mitral valve has two leaflets, and the triscupid valve has three. The aortic and pulmonary valves are referred to as "semilunar valves" because of the unique appearance of their leaflets, which are most aptly termed "cusps" and are shaped somewhat like a half-moon. The components of the mitral valve assembly include the mitral valve annulus; the anterior leaflet; the posterior leaflet; two papillary muscles which are attached at their bases to the interior surface of the left ventricular wall; and multiple chordae tendineae, which couple the mitral valve leaflets to the papillary muscles.

The problems that can develop with valves can be classified into two categories: (1) stenosis, in which a valve does not open properly, or (2) insufficiency, or regurgitation, in which a valve does not close properly.

Mitral regurgitation ("MR") is caused by dysfunction of the mitral subvalvular apparatus or direct injury to the valve leaflets. Multiple etiologies can lead to mitral regurgitation, with myxomatous degeneration of the valve and ischemic heart disease accounting for close to 60% of cases. Repair of the diseased valve requires major surgery on cardiopulmonary bypass to allow access to the valve. Consequently, some patients in the early or late stages of the disease are not considered appropriate candidates due to the high risk associated with the operation. Multiple studies have demonstrated that prosthetic replacement of the mitral valve can lead to significant postoperative left ventricular dysfunction and often requires lifelong treatment with anticoagulants. Mitral valve repair, using a posterior annuloplasty ring, has demonstrated improved results with better ventricular recovery. Nevertheless, recent studies performed by the inventors (Umana et al., Surg Forum 1997) have revealed that posterior ring annuloplasty causes changes in ventricular geometry that lead to paradoxical movement of the normal papillary muscles, further deteriorating ventricular performance. In contrast, the "bow-tie" repair in which the anterior and posterior leaflets of the mitral valve are fixed in opposition appears to enhance annular contractility while preserving ventricular architecture. This has resulted in improved postoperative ventricular function almost uniformly.

The present invention addresses the needs of all patients with mitral regurgitation without mitral stenosis, including those who heretofore may have been excluded due to having only moderate MR or being too sick to be candidates for major surgery.

The present invention finds utility not only for the repair of mitral valves but for all valves of the circulatory system, including aortic valves, tricuspid valves, and venous valves.

Techniques for improving the efficacy of corporeal valves are known. For example, Laufer et al., U.S. Pat. No. 5,609,598 describes a valving system for treatment of chronic venous insufficiency. The system has inherent limitations in terms of its effectiveness for the procedure described and its applicability, if any, to other valves, especially cardiac valves.

SUMMARY OF THE INVENTION

The present invention is directed to a method and apparatus for use in heart valve repair involving the use of an inserted device or grasper for grabbing and clasping together the anterior and posterior leaflets of the valve, by insertion into the left ventricle through the right chest via a thorascope, through the jugular vein, or through the femoral artery. The grasper will grab both leaflets, preferably after the heart has been stopped or slowed pharmacologically. The correctness of the initial grasp is assessed by, for example, intraoperative echocardiography, to ensure, for example, in the case of the mitral valve, that the mitral regurgitation is resolved. If not, the grasper will be able to "adjust" the leaflets to allow better coaptation or, if needed, re-grab the leaflets in a different location.

Either inherent to the grasper, as an integrally attached component, or as a separate device, a fastening device is introduced and a fastener is deployed to securely hold the leaflets in place after the grasper has been released. The remaining portion of the device, or optionally any separate device, is then removed.

Accessory devices needed for the procedure include instruments for thoracoscopic or percutaneous approaches. While the preferred method and apparatus described hereinbelow is discussed with reference to its use in connection with mitral valve repair, it is contemplated that the same or substantially similar apparatus and methodology would also be useful in repairing other valves found in the human circulatory systems, particularly other heart valves, such as, for example, venous valves, aortic valves and tricuspid valves, amongst others.

OBJECTS OF THE INVENTION

It is an object of the invention to provide a method for the repair of heart valves to increase their efficiency.

It is a further object of the invention to provide for a method for the repair of mitral valves to reduce mitral regurgitation.

It is also an object of the invention to provide for a method for the repair of the mitral valves which eliminates the need for cardiopulmonary bypass surgery.

It is a further object of the invention to provide for an apparatus for percutaneous insertion into the heart to effect the repair of a heart valve.

It is a yet further object of the invention to provide for the repair of a mitral valve by percutaneous insertion of a grasping and fastening device into the heart to repair a mitral valve and reduce or eliminate mitral regurgitation.

These and other objects of the invention will become apparent to one skilled in the art from the more detailed description given below.

BRIEF DESCRIPTION OF THE DRAWINGS

FIG. 5 is a schematic representation of an embodiment of the distal portion of an apparatus of the invention useful for grasping a mitral valve;

FIG. 6 is a schematic representation of an embodiment of a distal portion of an apparatus of the invention showing a configuration of a fastener holder and a fastener clip in the open position;

FIG. 7 is a schematic representation of an embodiment of FIG. 6 showing the release and closure of the fastener clip;

FIG. 11 is a detailed schematic representation of a preferred embodiment of the grasper device of the apparatus of the invention in the closed position with the integral closure means shown;

FIG. 12 is a detailed schematic representation of the preferred embodiment depicted in FIG. 9 showing the closure means piercing the leaflets of the valve;

FIGS. 14, 15, and 16 are partly cross-sectional schematic representations of another embodiment of the invention, wherein a self-closing closure is used;

FIG. 17 is a schematic representation of the self-sealing closure;

FIGS. 18 and 19 are schematic representations of an embodiment of the invention with a three-piece closure;

FIG. 20 is a schematic representation of an embodiment of the invention with a three-piece closure;

DETAILED DESCRIPTION OF THE INVENTION

Figure 1:
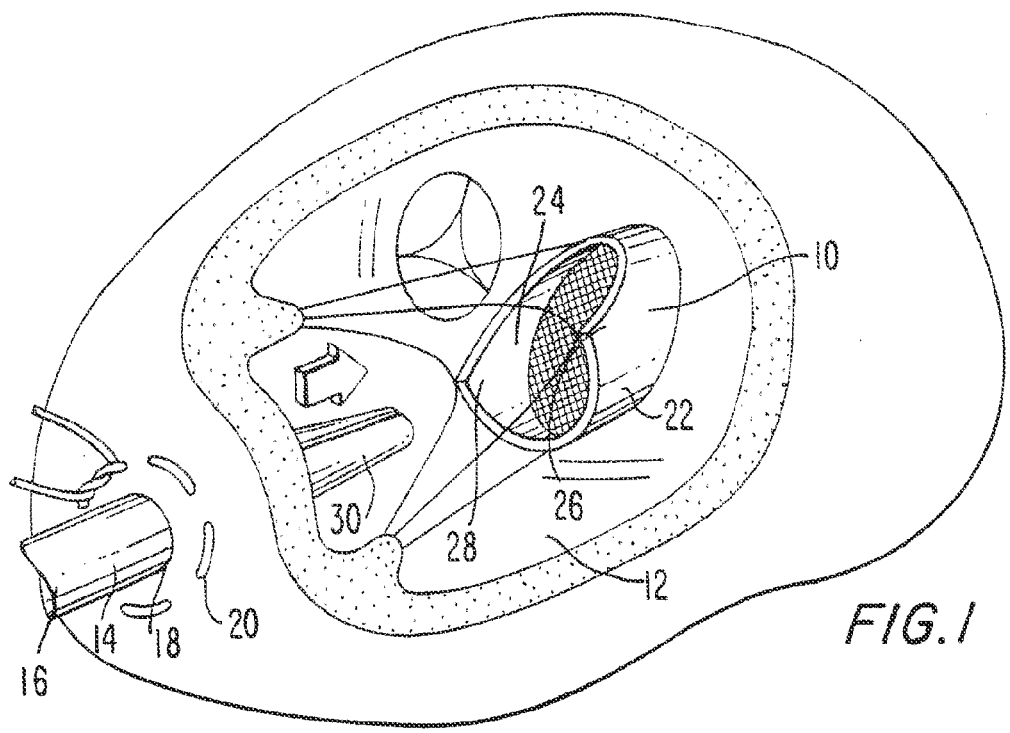
FIGS. 1 to 4 are each a schematic representation of a portion of the human heart showing the mitral valve, the left ventricle, and an apparatus of the invention in operation.

The invention can perhaps be better appreciated by making reference to the drawings. In FIG. 1 a portion of the human heart is depicted showing a mitral valve 10, a left ventricle 12 and the distal end 14 of a grasper apparatus of the invention 16, which has been inserted through an incision 18 in left ventricle 12. Incision 18 is loosely sutured with sutures 20 to loosely hold distal end 18 and to prevent bleeding.

Mitral valve 10 comprises anterior leaflet or cusp 22 and posterior leaflet or cusp 24, as well as two commissural cusps (pot shown). The primary intent of the invention herein is to secure the distal sections 26 and 28 of cusps 22 and 24, respectively, together or substantially adjacent.

Figure 2:
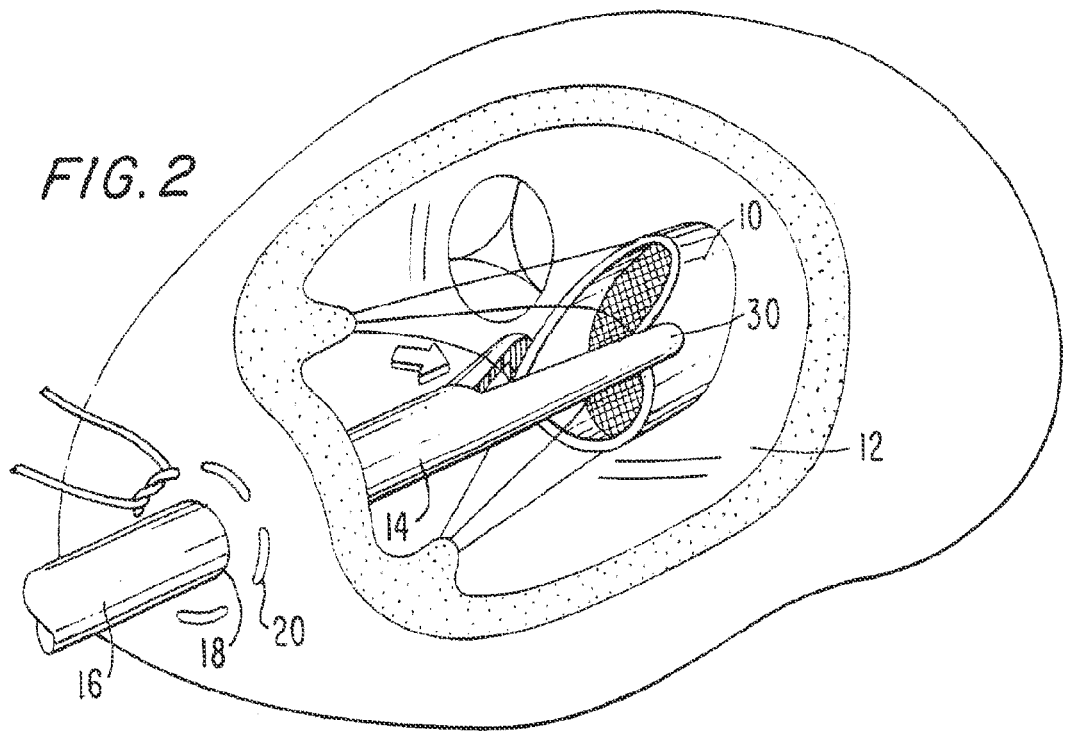
Figure 3:
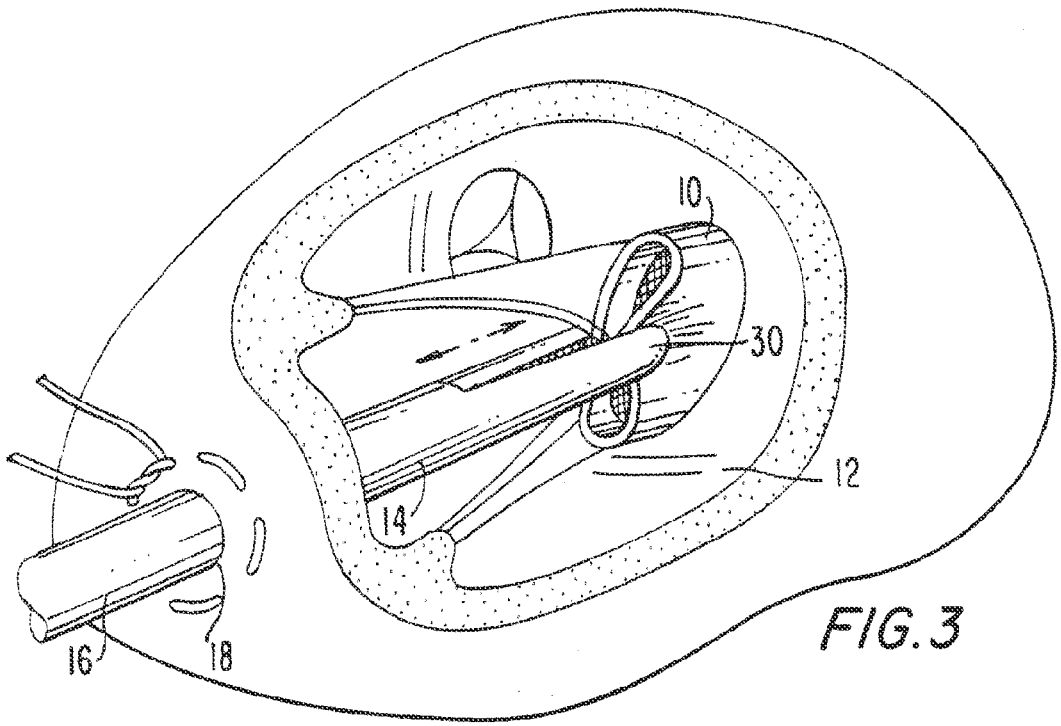
Figure 4:
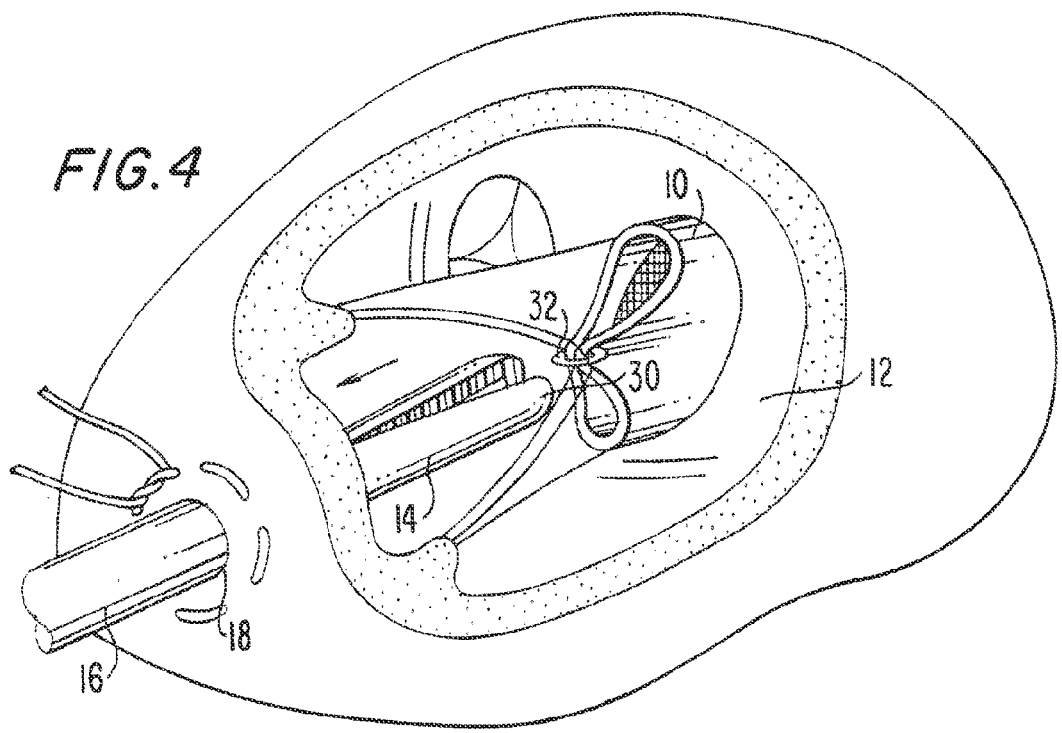

As can be seen in FIG. 2, the jaws 30 of distal end 14 are separated and positioned exterior to cusps 22 and 24. Then, as shown in FIG. 3, jaws 30 are clamped together to cause cusp distal sections 26 and 28 to come together. Once a closure is embedded, such as the loop closure 32 in FIG. 4, jaws 30 are opened slightly so that distal section 14 can be withdrawn.

The distal ends of the grasper means can vary greatly. It is contemplated that a variety of grasper means may be employed having differing grasper configurations and elements. For example, it is contemplated that the grasper means could be of the type wherein one side of the grasper is stationary and the other side movable. Alternatively, the grasper means might be of the type wherein both sides are movable in concert. Another alternative arrangement comprises a grasper means having multiple grasper elements to enable one to grasp and hold the leaflets of the valve in multiple locations. It is also contemplated that the grasper elements themselves might comprise one or more suction elements to secure and hold the valve leaflets in place. Preferably the grasper will have the capacity to adjust the leaflets of, for example, a mitral valve to obtain optimal coaptation.

In addition, it is contemplated that the grasper may comprise additional technology to facilitate the operation of the grasper. For example, the grasper may have echo doppler probe or a similar visualization technology that would allow even better localization of the leaflets and confirmation of ideal coaptation.

FIG. 5 depicts the grasper end 36 of a percutaneous apparatus 38 with jaws 40 in the open position. Jaws 40 of grasper end 36 are movably engaged about joint 42 such that the jaws may be easily and freely opened or closed by the operator of the percutaneous apparatus.

Depicted in FIG. 6 is an embodiment of the invention showing one possible configuration of a fastener holder 44 with a fastener clip 46 in place held in the open position for placement over the grasped leaflets of a mitral valve, The fastener holder 44 and fastener clip 46 may be integral with a grasper end as shown in FIG. 5 or separate from it, in which case it will be necessary to also provide a secondary percutaneous means for use in delivering and manipulating the fastener holder 44 and releasing and fixing the fastener clip 46 in the proper position about the leaves of a mitral valve, once they have been properly grasped by jaws 40 of grasper end 36.

FIG. 7 is a more detailed schematic representation of the fastener holder 44 with its jaws 48 in their open position and fastener clip 46 in place in the open position (dotted line), Also shown is fastener clip 46 in its released, closed position. Fastener clip 46, which may have a closed diameter of from about 3 to 7 mm, preferably about 5 ram, will be comprised of a suitable material such as stainless steel, nitinol, or titanium.

Figure 8:
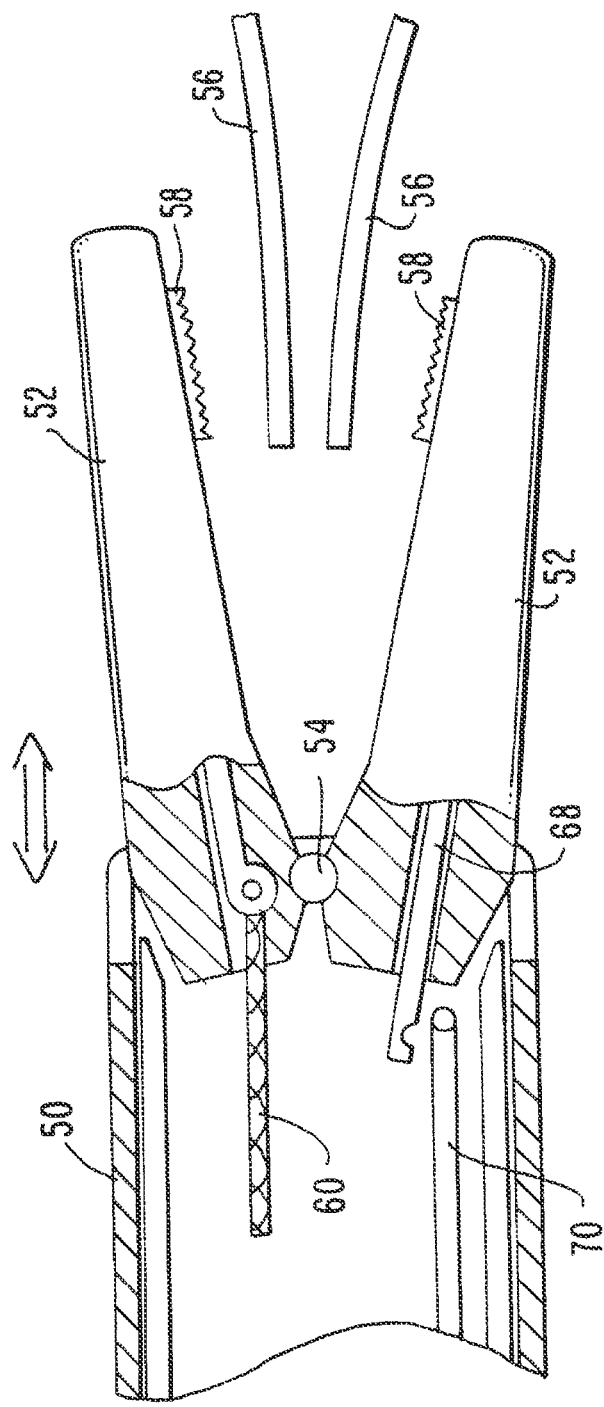
FIG. 8 is a detailed, partly cross-sectional schematic representation of the distal end of a preferred embodiment of a grasper device according to the invention in the open position.

FIG. 8 depicts a detailed, partly cross-sectional schematic representation of a preferred embodiment of the grasper device of the present invention, comprising grasper end 50, movable jaws 52 which are movably engaged about joint 54, in the open position, in proximity to valve leaflets 56. Each jaw 52 has a protruding grasping surface 58. However, the grasping surface 58 of one jaw 52 is operatively and slidably connected to a control member 60 to enable one to properly align valve leaflets 56, prior to fastening.

Figure 9:
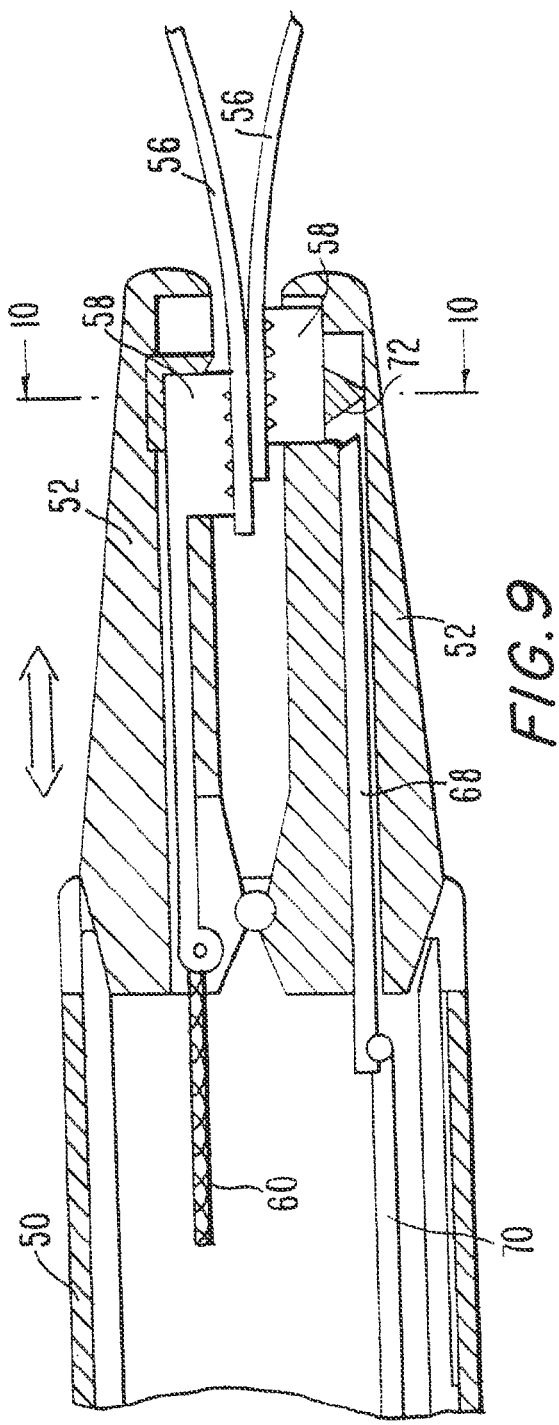
FIG. 9 is a detailed, partly cross-sectional schematic representation of the preferred embodiment of a grasper device according to the invention shown in FIG. 8 in a closed position depicting the translocated adjustable grasper and fastener anvil within the jaws.

In FIG. 9 the grasper device of the apparatus of the invention shown in FIG. 8 is in a closed position. Moveable jaws 52 have protruding grasper surfaces 58, which engage valve leaflets 56. Leaflets 56 are translocated to a more optimum position for fastening by the action of control member 60 on one of protruding grasping surfaces 58, as shown in FIG. 11. Also, stapler action rod 68 is now operatively connected to stapler control member 70.

Figure 10:
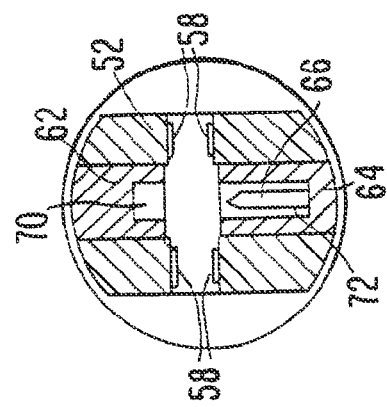
FIG. 10 is a cross-sectional representation across line 10-10 of the adjustable grasper shown in FIG. 9.

FIG. 10 is a schematic representation of a cross-section of the adjustable grasper depicted in FIG. 9. The jaws comprise grasper surfaces 58, an upper anvil 62 with recess 71, and a lower anvil 64 within which is located a staple type fastener 66 to effect the fastening of valve leaflets.

As shown in FIGS. 9, 11, and 12, lower anvil 64 has at least one slanted surface member 72. When stapler action rod 68 is forced distally against slanted surface member 72, stapler fastener 66 is forced through leaflets 56 into upper anvil 62 to close stapler fastener 66.

Figure 13:
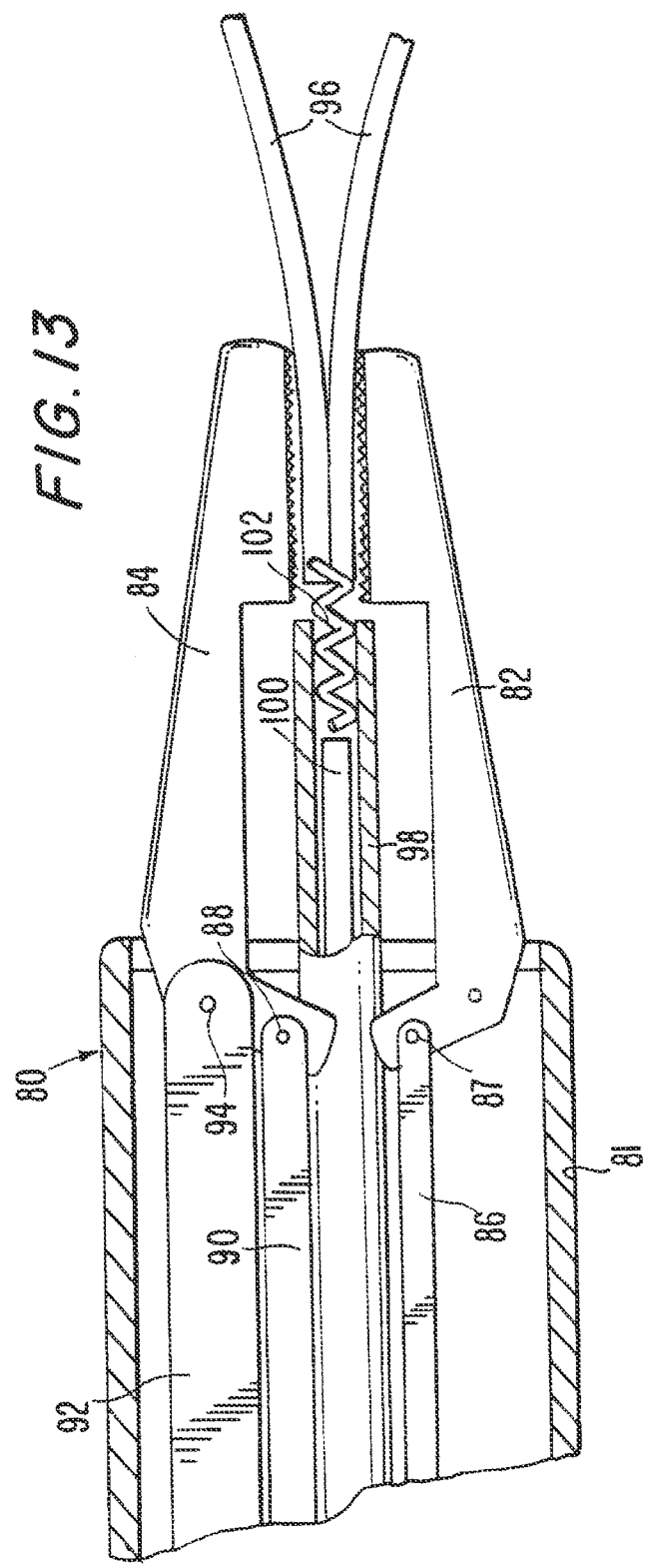
FIG. 13 is a detailed, partly cross-sectional schematic representation of yet another preferred embodiment of the distal end of a grasper device according to the invention showing the use of a coil closure means.

In another embodiment of the invention shown in FIG. 13, a grasper 80 comprises jaws 82, 84. Jaw 82 is movably connected to rod 86 at pivot point 87, and jaw 84 is movably connected at pivot point 88 to rod 90. Rod 92 is movably connected to jaw 84 at pivot 94. Operation of rods 90 and 92 causes jaws 82 and 84 to open and close on valve leaflets 96. Axial to grasper 80 is a sheath 98 containing a drive mechanism 100 for rotating coil fastener 102. Coil fastener 102 advances in a spiral mode piercing leaflets 96 in multiple locations as coil 102 is advanced into its final position.

Rods 86, 90, and 92 are each operatively connected to one or more control mechanisms (not shown). Also, distal section jaws 82, 84 may be slidable within grasper sheath 81.

Another device 110 of the invention is shown in FIGS. 14 to 16, where jaws 112 are operatively connected to a handle mechanism (not shown). Device 110 comprises a movable sheath 114 that contains a straightened closure fastener 116 that is capable of resuming or forming a circular shape to coapt valve leaflets (not shown). Device 110 has a slidably extruding grasping surface 118 that is operatively connected to the handle mechanism.

Once jaws 112 are closed, the distal tip of sheath 114 is advanced distally to be adjacent grasping surface 118 and its cooperating grasping surface 122. A pusher 124 coerces fastener 116 to advance out of the distal end 126 of sheath 114 to form a circular shape. Fastener 116 in this shape will coapt valve leaflets 120, as can be seen in FIG. 17.

The device 130 of the invention shown in FIGS. 18 and 19 is intended to form a three-piece closure device. Jaws 132 each removably hold a closure member 134 having a grasping surface 136. Located axially with device 130 is a closure crimper 138 that is removably fastened at the distal end 140 of a device rod 142. When jaws 132 grasp valve leaflets 144, closure crimper 138 is advanced distally by device rod 142 to fit over the proximal ends of closure members 134. The closure formed is shown in FIG. 20.

While a typical grasper means configuration would normally require the use of at least one control wire to actuate the grasper element(s), it is contemplated that multiple separate control wires could also be effectively employed and manipulated from the proximal end of the system to allow for the precise control of the individual grasper elements.

With regard to the fastening means employed, as noted above it is contemplated that the fastening means may be constituted as a single apparatus operating in concert with the grasper means. Alternatively, the fastening means may be constituted as an entirely separate device which is totally independent of the grasper means. More preferably the fastening means will be a separate device which will function using a monorail type system, wherein the fastening means will operate independently of the grasper means, but will ride via a loop over the same guidewire/catheter which houses and guides the grasper means.

While the preferred fastener depicted is in the form of a clip or staple, it is also contemplated that the fasteners employed to secure the leaflets of the valve may be of a variety of different configurations, each of which would function with greater or lesser effectiveness depending upon the operative conditions which prevail. In addition to clips or staples it is also contemplated that the following types of fasteners may also be effectively employed: coils, sutures, dual button fasteners, cufflink-like fasteners, and the like.

Suitable suture fasteners would include those which might require an appropriate mechanism to automatically suture tissue. Coil fasteners would generally be provided with sharpened ends to allow one to screw these fasteners into place by threading the sharpened end through the tissue of the valve leaflet.

Figure 21:
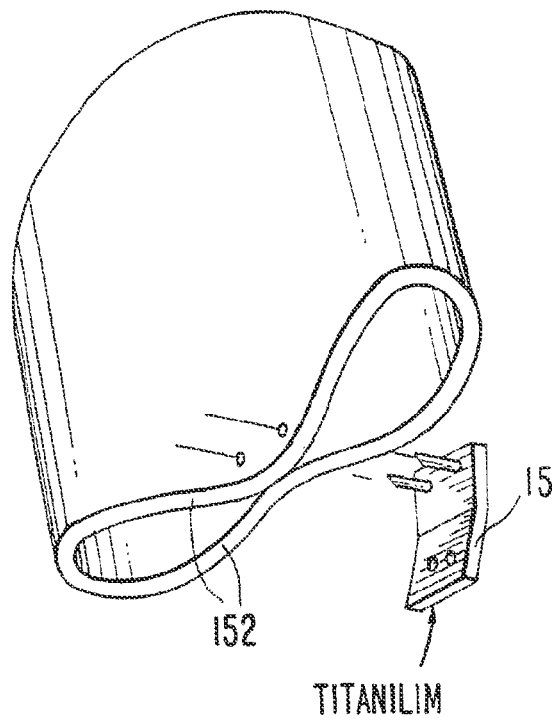
FIGS. 21 and 22 are oblique, schematic representations of a valve leaflet closure useful according to the invention.
Figure 22:
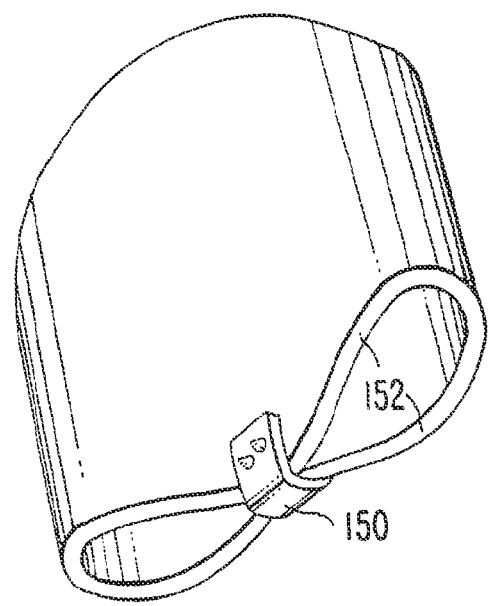
Figure 23:
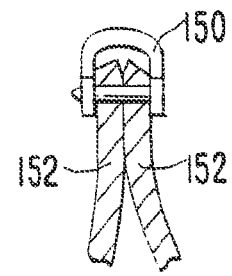
FIG. 23 is a partial cross-sectional view of the closure shown in FIGS. 21 and 22.

With reference to FIGS. 21 to 23 which depict a sequential representation of the closure of valve leaflets using one preferred closure means, shown in FIG. 22 is a clip type closure 150 being inserted through valve leaflets 152. FIG. 22 shows the clip type closure 150 in the fastened position. FIG. 23 is a cross-sectional view of the clip type closure 150 depicted in FIG. 23. Each closure 150 as shown in FIG. 21 would have a thickness of from about 0.5 to 1.8 mm, preferably about 1 mm, a width of from about 0.3 to 0.7 cm, preferably about 0.5 cm, and a length of from about 0.6 to 1.4 cm, preferably about 1 cm.

Figure 24:
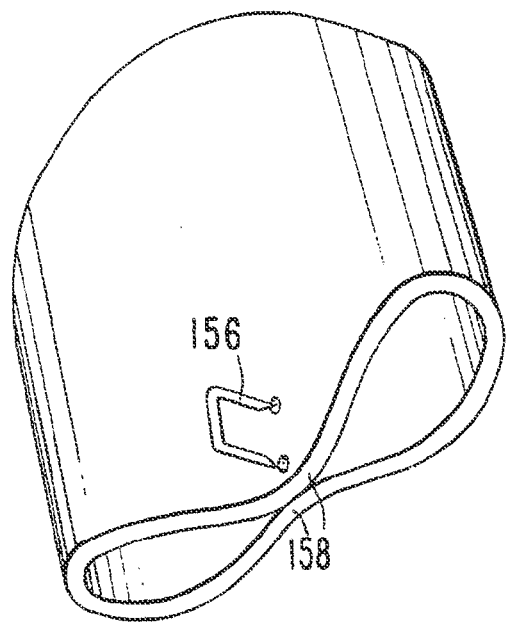
FIG. 24 is an oblique, schematic representation of another valve leaflet closure useful according to the invention.
Figure 25:
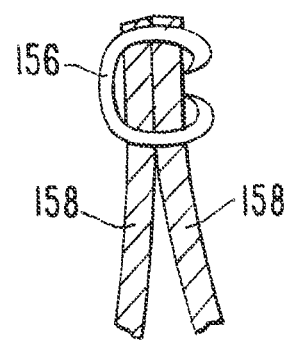
FIG. 25 is a partial cross-sectional view of the closure in FIG. 24 in position.
Figure 26:
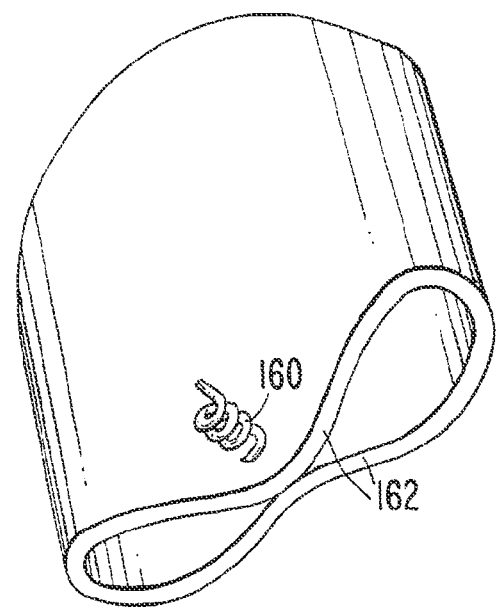
FIGS. 26 to 28 are each an oblique, schematic representation of a spiral coil valve leaflet closure useful according to the invention.

FIGS. 24 and 25 are each a schematic representation of the insertion of another preferred closure means of the invention. A staple-type closure 156 is inserted through valve leaflets 158, and then closed, as shown in FIG. 26. Closure 156 would preferably have an overall length (including sides) of from about 1 to 4 cm, preferably about 3 cm, an effective diameter of from about 0.1 to 0.5 mm, preferably about 0.3 mm, and an opening of from about 0.5 to 1.3 cm, preferably about 1 cm.

Figure 27:
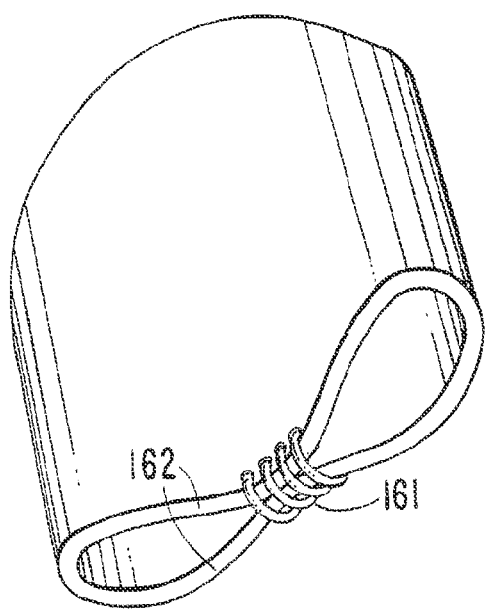
Figure 28:
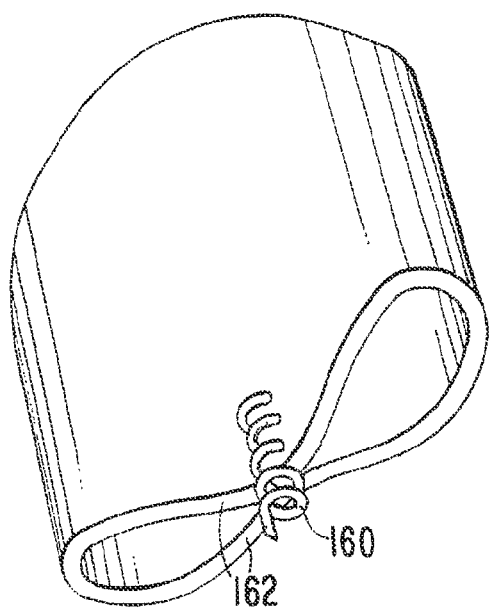

FIGS. 26 to 28 are each a schematic representation of the insertion of yet another preferred closure. A spiral coil closure 160 can be inserted across valve leaflets 162 in longitudinal, latitudinal, or transverse fashion, by use of, for example, the device shown in FIG. 13. Coils 160 will preferably have pointed ends and will have external dimensions comprising a length of from about 3 to 7 cm, preferably about 5 cm, and a diameter of from about 1 to 3 mm, preferably about 2 mm.

The overall diameter and/or the differential turns of coil 160 may be uniform or they may vary. For example, the diameter at each end of coil 160 could be the same as, greater than, or less than the diameter of the middle portion of the coil. Similarly, the ratio of the turns of the coil to the length, i.e., the pitch, could be consistent, or the pitch could be greater or less at each end of the coil. The diameter of the coil wire will preferably be consistent.

Each coil 160 would have a length of from about 3 to 7 cm, preferably about 5 cm, with a diameter of from about 1 to 3 mm, preferably about 2 mm, and a coil wire diameter of from about 0.2 to 0.4 mm. The winding of coil 160 should be from about 5 to 10 turns/cm in an unstressed condition.

Figure 29:
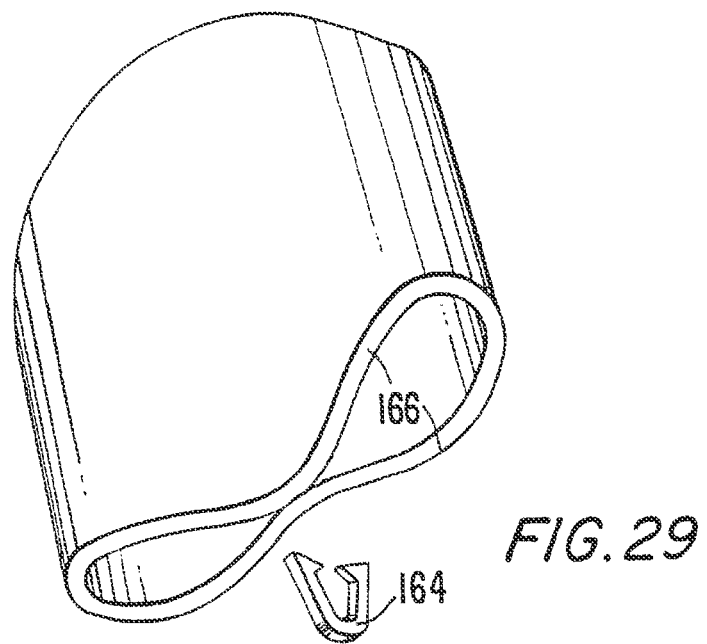
FIG. 29 is an oblique schematic representation of a U-shaped valve leaflet closure useful according to the invention.
Figure 30:
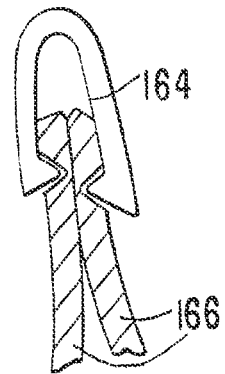
FIG. 30 is a partly cross-sectional view of the closure shown in FIG. 29.

In FIGS. 29 and 30 a U-shaped barbed clip-type closure 164 is applied to leaflet 166.

The device and fasteners used according to the invention must be comprised of biocompatible, nonimmunogenic materials. The grasper is preferably comprised of rigid materials such as titanium, nitinol, stainless steel, or rigid polymeric material such as polyethylene or polyurethane. The clips, staples, coils, etc., are preferably comprised of titanium, nitinol, or stainless steel. In some instances fasteners comprised of molded polymeric material may also be useful.

There are four different approaches which one might take to effect a repair of the mitral heart valve according to the invention:

Such a procedure might be undertaken while the patient is on by-pass with an open-chest, either transapically or transatrially. A median sternotomy is performed, and the patient is placed on cardiopulmonary bypass by cannulating the ascending aorta and the right atrium. A purse-string suture is then placed on the apex of the left ventricle, and a stab incision is performed to insert the instrument which will grasp and attach the mitral valve leaflets. Once adequate repair of the valve is attained, the instrument is removed and the air evacuated from the left ventricle through the apical incision. The ventricle is then repaired using conventional wound closure techniques.

Alternatively, the grasper can be introduced through a similar stab incision performed over the roof of the left atrium. The grasper will cross the valve and then be manipulated to revert to grasp the leaflets from the atrial side and place the suturing device, just as postulated from the transventricular approach, Once adequacy of repair is confirmed, the device is extracted and the atriotomy closed using conventional wound closure techniques.

This procedure can alternatively be performed with the patient off bypass, through either a left or right thoracotomy or a sternotomy incision. The technique would be similar to that outlined for repair of mitral regurgitation on cardiopulmonary bypass. After opening the chest, the patient is placed on medication (beta-blocker) to slow the heart rate to approximately 40 beats per minute, This allows adequate echocardiographic visualization of the leaflets in order to grasp and attach them.

Third, such a procedure can be undertaken thorascopically. The patient is intubated selectively in order to collapse the left lung, and percutaneous ports are inserted into the left chest, allowing visualization of the apex of the heart or left atrium. Through a separate port, the device is introduced into the thoracic cavity and subsequently into the left ventricle through the apex. Previously, a purse-string or triangular suture had been placed around the tip of the ventricle to control bleeding around the ventricular entry site. Subsequent steps of the repair are identical to those described for patients with an open chest, off bypass.

Should the operation require the patient to be placed on bypass, this can be attained percutaneously from the groin by cannulating the femoral artery and vein. This technique could prove particularly useful in the early stages of development of the technique, since the surgeon would be able to operate on a decompressed heart and slow or cease the heart rate as needed, without hemodynamic compromise.

Lastly, a percutaneous approach to repair of the mitral valve would be possible with this invention by inserting the device either through the femoral artery or jugular vein. When the former is used, the left ventricle is reached by placing the device across the aortic valve. The leaflets will be grasped by turning the tip of the instrument approximately 160° from the entry angle. As previously stated, the grasper's tips are adjusted to obtain optimal apposition and the suturing device delivered. If a transvenous approach is employed, the left atrium is entered through the interatrial septum and the leaflets are handled as described for the transatrial technique.

To determine the relative efficacy of the method of the invention in effecting the repair of heart valves such as mitral valves a number of procedures were performed on both animal and human test subjects as follows:

Animal Testing

Six adult sheep underwent ligation of 0M2 and 0M3 through a left thoracotomy to induce chronic ischemic MR. After 8 weeks, animals were placed on cardiopulmonary bypass. Using a posterior approach to the left atrium, a bow-tie repair was performed. A posterior suture annuloplasty (DeVega) served as control. Snares were placed on both repairs to allow alternate tightening during measurements. Ten 2-mm piezo-electric crystals were sutured around the MV annulus and at the bases and tips of the papillary muscles. Six crystals were secured to the apex (1), septum (1), and epicardial short axis of the left ventricle (4) for 3-dimensional sonomicrometry array localization (3D-

SAL) imaging. 3D-SAL measurements were performed after weaning from cardiopulmonary bypass at baseline and with each type of repair. Echocardiography was used to measure MR, MV area, and fractional shortening.

TABLE 1

MR, mitral valve area, and fractional shortening

|  | MR | FS | MVA (cm$^2$) |
|---|---|---|---|
| Baseline | 3.3 | 0.46 | 5.4 |
| DeVega | 1.4 | 0.53 | 3.9 |
| Bow-tie | 1.2 | 0.57 | 3.3 |

FS = fractional shortening;
MVA = mitral valve area (planimetry).
P = 0.0159 vs. baseline
**P = 0.0079 vs. baseline As shown from the results presented in Table 1, MR decreased significantly with both repairs compared with baseline. Post-operative improvements in fractional shortening was greater in the bow-tie group but did not reach statistical significance. MVA, measured by planimetry, decreased more with the bow-tie repair; nevertheless, the resultant areas were still substantial without evidence of a transvalvular gradient. Mitral valve annular contractility (% area change=(maximum area−minimum area)/maximum area) by 3D-SAL increased from 19.7%±4.0% at baseline to 21.5%±3.2% after bow-tie repair (P=0.026). Suture annuloplasty decreased annular contractility to 15.7%±3.6% (P=0.0011 vs. baseline, and P=0.0001 vs. bow-tie).

The results obtained suggest that current techniques of mitral valve repair in ischemic MR may further impair left ventricular performance by limiting systolic function of the annulus and base of the heart. The bow-tie repair technique which is the subject of the present invention controls MR and directly addresses subvalvular dysfunction resulting in improved annular and left ventricular function.

Human Testing

The charts of eleven patients (five males and six females) undergoing mitral valve repair in conjunction with a central leaflet suture ("bow-tie" repair) reviewed. Patients were operated on between August 1996 and April 1997. Mean age was 68 years (range, 44 to 78). Etiology of mitral regurgitation (MR) was ischemic in nine patients and degenerative in two, Mitral regurgitation was attributed to ischemia if any of the following criteria proposed by Radford et al. was met: (1) rupture of a papillary muscle chord or head (n=3); (2) infarction of the papillary muscle in the absence of leaflet pathology (n=3); (3) clear history of new onset or worsening of mitral regurgitation after documented myocardial infarction (n=3).

The diagnosis of MR was established by echocardiography in 10/10 patients, and semiquantitatively graded as severe (4+), moderate/severe (3+), mild/moderate (2+), mild (1+), and trace. Left-sided cardiac catheterization confirmed the presence of MR in nine patients and the presence of critical coronary artery disease (CAD) invariably involving the circumflex and posterior descending artery territories in all patients with ischemic MR. Preoperative diagnoses and hemodynamics obtained during catheterization are shown in Table 2. All patients were in NYHA class III or IV at the time of surgery.

TABLE 2

Preoperative diagnosis and hemodynamics.

| Patient | Diagnosis | Age | CO | PCWP | v-wave |
|---|---|---|---|---|---|
| 1 | Unstable angina | 59 | 4.2 | 30 | 80 |
| 2 | CAD/torn post. chord | 78 | 2.4 | 6 | 10 |
| 3 | CAD | 74 | n/a | 14 | 15 |
| 4 | CAD/MIx3 | 64 | n/a | n/a | n/a |
| 5 | Unstable angina/MIx2 | 44 | 4.0 | 26 | 41 |
| 6 | Ischemic VSD | 77 | 4.0 | 28 | 21 |
| 7 | AI/MR | 77 | 4.5 | 29 | 39 |
| 8 | CAD/APM rupture | 67 | 4.3 | 27 | 65 |
| 9 | CAD/V-tach arrest | 71 | 4.1 | 20 | 28 |
| 10 | Degenerative MR | 70 | 3.5 | 20 | 21 |
| 11 | AMI/PPM rupture | 67 | 4.1 | 33 | 60 |

AI-aortic insufficiency; AMI-acute myocardial infarction; APM-anterior papillary muscle; CAD-coronary artery disease; post-posterior; PPM-posterior papillary muscle; VSD-ventricular septal defect; v-tach-ventricular tachycardia With the patient under anesthesia, the valve is visualized on transesophageal echocardiogram (TEE) and the likely mode of failure determined, with special emphasis on the presence of leaflet prolapse and site and direction of the regurgitant jet. After the heart was stopped, a bulb syringe with cold saline is used to distend the left ventricle and confirm the mode of valve failure. A conventional repair using an annuloplasty right is generally performed and the valve is reinspected with saline injection.

If the leaflet edges do not oppose each other in a concentric circle parallel to the annuloplasty ring, and continued regurgitation is observed, then a "bow-tie" repair is initiated. If the repair is performed from the transventricular or transaortic exposure, a single figure of eight 4-0 prolene suture is placed without screening leaflet eight 4-0 prolene suture is placed without screening leaflet-coaptation. Using a 4-0 prolene suture, the anterior leaflet is attached to the corresponding posterior leaflet at the site of malapposition. The FIG. 8 suture is placed through each leaflet just as the edge turns down to attach to the primary chordae. This is usually the most cephalad site where the two leaflets would touch during systole and creates the largest area of coaptation possible.

At times the suture is very close to a commissure, and the result is a narrowing of single valve orifice. More commonly, the suture is closer to the center of the valve and a double orifice valve is created which resembles a "bow-tie". After visual confirmation that the repair is satisfactory with cold saline injection, the atrium is closed, the patient weaned from CPB, and an intraoperative TEE used to confirm the adequacy of the repair. Standard as well as exercise transthoracic echocardiograms were performed prior to discharge to establish the competency of the "bow-tie" repair as well as the absence of a significant gradient across the valve.

Six patients were operated on electively for worsening MR leading to intractable congestive heart failure or unstable angina. Four patients underwent emergent operation due to acute worsening of MR secondary to ischemic anterior papillary muscle rupture (n=2), acute MI with cardiogenic shock requiring intraaortic counterpulsation balloon, severe MR and malignant arrhythmias (N=1), and acute worsening of chronic degenerative MR (n=1). One patient had moderate (3+0) MR in association with critical aortic insufficiency. Mean degree of preoperative MR by echo was 3.5±0.7, with mean ejection fraction (SF) of 42%±17%. Nine patients underwent preoperative cardiac catheterization. Mean pulmonary capillary wedge pressure was 23 mm Hg±8 mm Hg, with mean atrial v-wave of 39 mm Hg±25 mm Hg; mean CO as measured by thermodilution technique was 3.9 l/min (range 2.4 to 4.5 l/min) (Table 2). Concomitant procedures performed at the time of MR included coronary artery bypass grafting (CABG) in eight patients. Of the two patients with a degenerative etiology of valvular disease, one required aortic valve replacement, whereas the second underwent posterior leaflet quadrangular resection and annuloplasty. Two patients, not included in this series, with end-stage congestive heart failure (CHF) secondary to ventricular dilation had "bow-tie" repairs during partial left ventriculectomy. Nine patients had a posterior ring annuloplasty as primary procedure for treatment of MR (Table 3). One patient required repair of ischemic ventricular septal defect (VSD) through a ventriculotomy, which made insertion of an annuloplasty ring impractical. This patient's mitral valve was successfully repaired with a "bow-tie" alone. A second patient presented with acute MR secondary to rupture of the anterior head of the ppm. Repair of the papillary muscle was performed using pericardial pledgets. Due to the lack of annular dilatation and persistence of MR a "bow-tie" suture was placed without an annuloplasty ring. Control of MR assessed intraoperatively by direct cold saline injection and TEE was satisfactory in all patients.

TABLE 3

Operative indications and concomitant procedures

| Patient | Operative indication | Other procedures |
|---|---|---|
| 1 | MR, unstable angina | CABG, C-E #28 |
| 2 | Torn post chord, MR | Post quad resection, C-E #32 |
| 3 | CAD, MR | CABG, C-E #32 |
| 4 | CAD, MR | CABG, C-E #30 |
| 5 | Unstable angina, MR | CABG, C-E #28 |
| 6 | Ischemic VSD, MR | CABG |
| 7 | Critical AI, MR | AVR, C-E #30 |
| 8 | CAD, ALM rupture, MR | CABG, C-E #26 |
| 9 | CAD, MR | CABG, C-E #28 |
| 10 | MR, CHF | C-E #30 |
| 11 | PPM rupture, MR | CABG, primary PPM repair |

AVR—aortic valve replacement;
C-E Cosgrove ring;
CHF congestive heart failure;
PPM posterior papillary muscle It will thus be seen that the objects set forth above, among those made apparent from the preceding description, are efficiently attained and, since certain changes may be made in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

| DRAWING COMPONENTS | |
|---|---|
| No. | Component |
| 10 | mitral valve |
| 12 | left ventricle |
| 14 | distal end of grasper |
| 16 | grasper |
| 18 | incision |

| DRAWING COMPONENTS-continued | |
|---|---|
| No. | Component |
| 20 | suture |
| 22 | anterior leaflet or cusp |
| 24 | posterior leaflet or cusp |
| 26 | anterior cusp distal section |
| 28 | posterior cusp distal section |
| 30 | jaw |
| 32 | closure loop |
| 36 | grasper end |
| 38 | percutaneous apparatus |
| 40 | jaw |
| 42 | joint |
| 44 | fastener holder |
| 46 | fastener clip |
| 48 | jaw |
| 50 | grasper end |
| 52 | jaw |
| 54 | joint |
| 56 | valve leaflet |
| 58 | protruding grasping surface |
| 60 | control number |
| 62 | upper anvil |
| 64 | lower anvil |
| 66 | staple type fastener |
| 68 | staple action rod |
| 71 | recess |
| 72 | anvil slanted surface |
| 80 | grasper |
| 81 | grasper sheath |
| 82 | jaw |
| 84 | jaw |
| 86 | rod |
| 87 | pivot point |
| 88 | pivot point |
| 90 | rod |
| 92 | rod |
| 94 | pivot |
| 96 | valve leaflet |
| 98 | sheath |
| 100 | drive mechanism |
| 102 | coil fastener |
| 110 | grasper device |
| 112 | jaw |
| 114 | sheath |
| 116 | fastener |
| 118 | grasping surface |
| 120 | leaflet |
| 122 | cooperating grasping surface |
| 124 | pusher |
| 130 | grasper device |
| 132 | jaw |
| 134 | closure member |
| 136 | grasping surface |
| 138 | closure crimper |
| 140 | rod distal end |
| 142 | device rod |
| 144 | valve leaflet |
| 150 | clip-type closure |
| 152 | valve leaflet |
| 156 | staple-type closure |
| 158 | valve leaflet |
| 160 | spiral closure |
| 162 | valve leaflet |
| 164 | barbed-clip closure |
| 166 | valve leaflet |

What is claimed is:

1. A valve repair apparatus for percutaneously repairing a heart valve having leaflets, the valve repair apparatus comprising:
   an insertion device comprising a first jaw with a first grasping surface and a second jaw with a second grasping surface, the first and second grasping surfaces being capable of releasably grasping the leaflets,
   the first jaw pivotably connected to a first rod, the second jaw pivotably connected to a second rod,
the second jaw pivotably connected to a third rod;
a coil fastener adapted for coupling the leaflets together; and
a drive mechanism configured to advance the fastener into the leaflets.

2. The apparatus of claim 1, wherein the drive mechanism is configured to rotate the coil fastener.

3. The apparatus of claim 1, wherein operation of the second rod and third rod actuate the first and second jaw to grasp the leaflets.

4. The apparatus of claim 1, further comprising a sheath disposed axially of the drive mechanism.

5. The apparatus of claim 4, wherein the fastener is at least partially disposed within the sheath.

6. The apparatus of claim 1, wherein the first jaw is pivotably connected to the first rod at a proximal end of the first jaw.

7. The apparatus of claim 1, wherein the second jaw is pivotably connected to the second rod at a proximal end of the second jaw.

8. The apparatus of claim 1, wherein the second jaw is pivotably connected to the third rod at a proximal end of the second jaw.

9. The apparatus of claim 1, wherein sliding movement of the second and third rod pivot the jaws into an open position.

10. The apparatus of claim 1, wherein the grasping surface of the first jaw is dispose at a distal end of the first jaw.

11. The apparatus of claim 1, wherein the grasping surface of the second jaw is disposed at a distal end of the second jaw.

12. The valve repair apparatus of claim 1, wherein the first and second jaws are retractable within a lumen of a sheath.

13. The apparatus of claim 1, further including a fastener holder, wherein the fastener holder includes a tubular sheath.

14. The apparatus of claim 13, wherein the fastener holder further includes a slidable push rod contained within the tubular sheath and operatively connected to a fastener contained within the tubular sheath.

15. The apparatus of claim 14, wherein the push rod is slidable distally to advance a fastener out of the distal end of the tubular sheath.

16. The apparatus of claim 1, wherein the first and second jaws are operatively connected to a handle mechanism.

17. The valve repair apparatus of claim 16, wherein the handle mechanism is operatively connected to the first and second rods.

* * * * *